(12) United States Patent
Tsaur

(10) Patent No.: US 6,811,339 B1
(45) Date of Patent: Nov. 2, 2004

(54) MULTIPLE APPLICATORS

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 10/693,426

(22) Filed: Oct. 24, 2003

(51) Int. Cl.$^7$ .......................... B43K 27/02; B43K 5/14; B65D 6/00
(52) U.S. Cl. .......................... 401/18; 401/17; 401/132; 220/4.07; 220/23.4
(58) Field of Search ............................ 401/17, 18, 57, 401/132; 220/4.07, 4.06, 23.4; 206/430, 503, 504, 508

(56) References Cited

U.S. PATENT DOCUMENTS 3,184,054 A * 5/1965 Kuhlman ................... 206/419
5,904,263 A * 5/1999 St. Pierre et al. .......... 220/23.4
6,612,764 B2 * 9/2003 Dumler et al. ................ 401/18

* cited by examiner

Primary Examiner—David J. Walczak
(74) Attorney, Agent, or Firm—Joe Nieh

(57) ABSTRACT

A multiple applicators comprising an elongated housing that is separated into multiple sealed compartments containing a liquid and an applicator tip with a score line formed at each of the sealed compartments located near the applicator tip wherein the elongated housing may be selectively severed into shorter sections at the score lines and removed. The removed section of the elongated housing is used to apply the liquid or viscous substance contained therein and disposed of after application. The remainder of the elongated housing with the remaining unused applicator tips and liquid is retained for subsequent uses.

24 Claims, 2 Drawing Sheets

MULTIPLE APPLICATORS

BACKGROUND

1. Field of Invention

The present invention relates generally to a sealed container. More specifically the present invention relates to a sealed container of multiple applicators that may be removed and used one at a time.

BACKGROUND

2. Description of Related Art

Applicators such as cotton swabs are generally used to apply medication, anesthetic, alcohol, and various other liquids and viscous substances such as creams. Swab applicator generally comprises of a tubular handle with a formed absorbent tip at one or both ends of the tubular handle. The absorbent tip may be made of cotton or a foam absorbent material. The tip may also be a brush. The tubular handle may be made of wood, paper, or plastic and it may be solid or hollow.

Generally the applicator tip of a dry swab applicator is first placed in contact with the liquid to be applied for the applicator tip to absorb the liquid. Subsequently, the moisturized applicator tip is placed in contact with the surface to apply the absorbed liquid to the surface. Swab applicators may also be pre-moistened with the desired liquid or viscous substance such as a cream and sealed in a container for subsequent use. Generally the pre-moistened swab applicators are packaged individually so that opening the packaging to retrieve one swab applicator will not affect the remaining swab applicators.

SUMMARY OF THE INVENTION

The present invention is a sealed container of multiple applicators that may be selectively opened and removed one at a time. The multiple applicators comprises of an elongated housing that is separated into multiple sealed compartments containing a liquid or a viscous substance with a score line formed at each of the sealed compartments wherein the elongated housing may be selectively severed into shorter sections at the score lines and removed. In the preferred embodiment, each of said sealed compartments also encloses an applicator tip such as a swab applicator affixed within the sealed compartment with the applicator tip disposed near the score line. The removed section of the elongated housing is used to apply the liquid or viscous substance contained therein and disposed of after application. The remainder of the elongated housing with the remaining unused applicator tips and liquid or viscous substance is retained for other applications or for subsequent uses.

DETAILED DESCRIPTION OF THE PREFERRED EMBODIMENT

Figure 1:
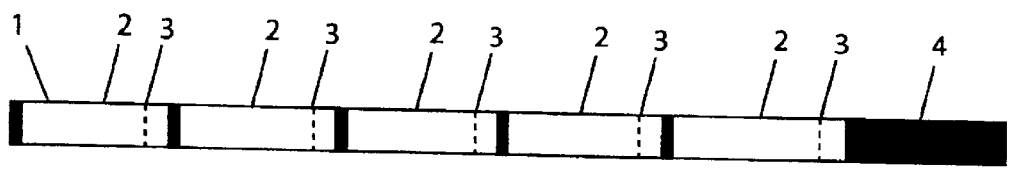
FIG. 1 shows the preferred embodiment of the multiple applicators.

FIG. 1 shows the preferred embodiment of the present invention. In the preferred embodiment, the multiple applicators comprises of an elongated housing 1 that is separated into multiple sealed compartments 2 along its length. Each of the sealed compartments 2 may be either dry or contains a liquid or a viscous substance. A score line 3 is formed at each of the sealed compartments 2 wherein each sealed compartment 2 may be snapped open and removed at the score line 3. The elongated housing 1 may be selectively severed into shorter sections at the score lines 3 and removed. In the preferred embodiment, one end 4 of the elongated housing 1 may be extended beyond the sealed end of the last sealed compartment to act as a handle for the user to hold such that the last sealed compartment may be snapped open at the score line easily. After the sealed compartment is snapped open and used, it may be disposed of while the remainder of the elongated housing with the remaining unused sealed compartments and any liquid or viscous substance within them are retained for other applications or for subsequent uses.

The elongated housing 1 may be of any desire length with multiple sealed compartments 2 of any desired length along its length. The elongated housing 1 may also be straight or curved. When the elongated housing 1 is curved, it may be formed into a spiral and allows easy and compact storage and transportation.

Figure 2:
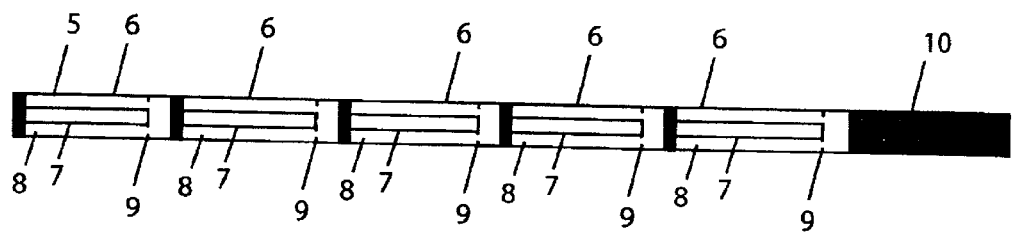
FIG. 2 shows another embodiment of the multiple applicators.

FIG. 2 shows another embodiment of the present invention. In this embodiment the multiple applicators comprises of an elongated housing 5 that is separated into multiple sealed compartments 6 along its length. One or more of the sealed compartments encloses an elongated member 7 with one end affixed to one end of the sealed compartment 6 and contains a liquid 8. A score line 9 is formed at each of the sealed compartments 6 near the free end of the elongated member 7 wherein the sealed compartment 6 may be snapped open and removed at the score line 9.

When the diameter of the elongated housing 5 is reduced to a dimension such that the liquid 8 will not reliably flow out of the compartment 6 due to its surface tension, the elongated member 7 will increase the capillary action and disrupt the surface tension of the liquid 8 contained within the sealed compartment 6 and allow the liquid 8 to reliably flow out of the sealed compartment 6 once it is snapped opened. The elongated housing 5 may be selectively severed into shorter sections at the score lines 9 and removed. One end 10 of the elongated housing 5 may be extended beyond the sealed end of the last sealed compartment to act as a handle for the user to hold such that the last sealed compartment may be snapped open at the score line easily. After the sealed compartment 6 is snapped open and used, it may be disposed of while the remainder of the elongated housing with the remaining unused sealed compartments and any liquid or viscous substance within them are retained for other applications or for subsequent uses.

Figure 3:
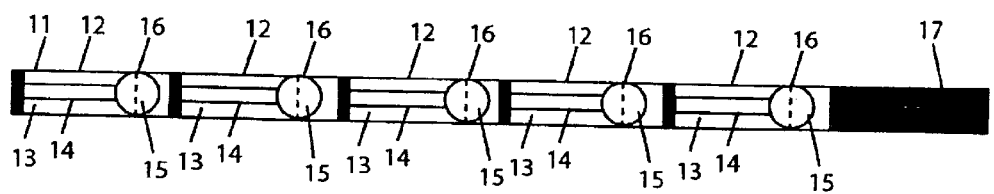
FIG. 3 shows another embodiment of the multiple applicators.
Figure 4:
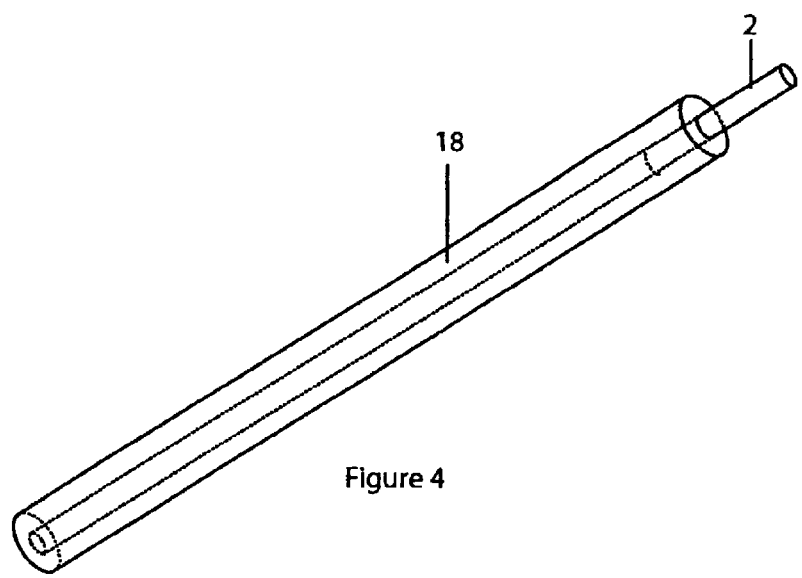
FIG. 4 shows a hollow tube as the holder.
Figure 5:
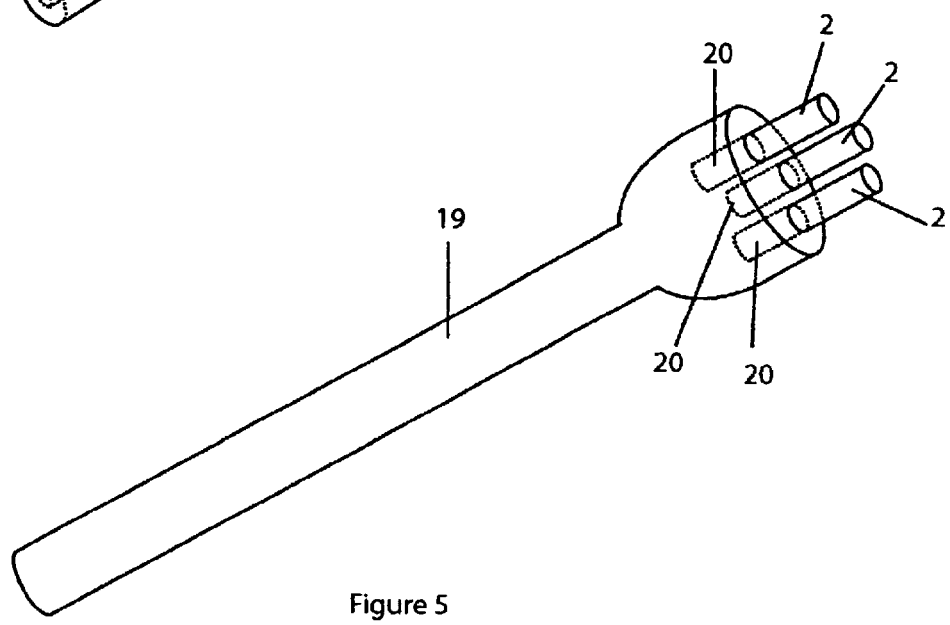
FIG. 5 shows the holder as a solid tube with multiple holes at its end.

FIG. 3 shows yet another embodiment of the present invention. In this embodiment the multiple applicators comprises of an elongated housing 11 that is separated into multiple sealed compartments 12 along its length. One or more of the sealed compartments 12 encloses a liquid 13 or a viscous substance and an elongated member 14 with one end affixed to one end of the sealed compartment 12 and an applicator tip 15 affixed to its free end. A score line 16 is formed at each of the sealed compartments 12 near the applicator tip 15 wherein the sealed compartment 12 may be snapped open and removed at the score line 16. After removal, the applicator may be used to apply the liquid 13 or viscous substance within it.

When the diameter of the elongated housing 11 is reduced to a dimension such that the liquid 13 will not reliably flow out of the compartment due to its surface tension, the elongated member 14 will increase the capillary action and disrupt the surface tension of the liquid 13 contained within the sealed compartment 12 and allow the liquid 13 to reliably flow out of the sealed compartment 12 and into the applicator tip 15 once it is snapped opened. The elongated housing 11 may be selectively severed into shorter sections at the score lines 16 and removed. One end 17 of the elongated housing 11 may be extended beyond the sealed end of the last sealed compartment to act as a handle for the user to hold such that the last sealed compartment may be snapped open at the score line easily. After the sealed compartment is snapped open and used, it may be disposed of while the remainder of the elongated housing with the remaining unused sealed compartments and any liquid or viscous substance within them are retained for other applications or for subsequent uses.

Various combinations of the above disclosed multiple applicators are possible. For example, elongated housing may contain multiple sealed compartments with various combinations of dry, wet, elongated member, or applicator tips. The sealed compartments may all have the same content or may have various combinations of contents within them.

Furthermore, an optional holder may be used to hold the removed applicator section if a longer length is desired. The holder may be a hollow tube 18 or a solid tube 19 with one or more holes 20 at its end that will slide over the removed applicator section 2 and retain it in the hollow end or one of the holes 20 for application. The holder 18, 19 may also be a hollow end of the elongated housing that extends beyond the sealed end of the last sealed compartment. After application, the removed applicator 2 may be detached from the holder 18, 19 and disposed. The holder 18, 19 may be re-used to hold the next applicator section 2.

Although the description above contains many specificities, these should not be construed as limiting the scope of the invention but as merely providing illustrations of some of the presently preferred embodiments of this invention. Thus the scope of the invention should be determined by appended claims and their legal equivalents, rather than by the examples given.

What is claimed is:

1. A multiple applicators comprising:
    an elongated housing that is separated into multiple sealed compartments along its length; and
    an opening means located at one or more of said sealed compartments near an end of said sealed compartment away from the end near the opening means in the adjacent sealed compartments wherein said sealed compartment may be opened and removed;
    wherein said elongated housing may be selectively severed into shorter sections at the opening means.

2. A multiple applicators as in claim 1, wherein a holder is provided comprising an elongated hollow tube or an elongated member with one or more holes at its end to hold the severed section of the elongated housing for application.

3. A multiple applicators comprising:
    an elongated housing that is separated into multiple sealed compartments along its length; and
    an opening means in the form of a score line located at one or more of said sealed compartments wherein said sealed compartment may be opened and removed;
    wherein said elongated housing may be selectively severed into shorter sections at the opening means.

4. A multiple applicators as in claim 3, wherein one or more of said sealed compartments enclose a liquid or a viscous substance.

5. A multiple applicators as in claim 3, wherein said elongated housing further comprises of one end that extends beyond the sealed end of the last sealed compartment wherein the extended section of the elongated housing acts as a handle for the user to hold such that the last sealed compartment may be opened easily.

6. A multiple applicators as in claim 1, wherein one or more of said sealed compartments enclose a liquid or a viscous substance.

7. A multiple applicators as in claim 6, wherein said elongated housing further comprises of one end that extends beyond the sealed end of the last sealed compartment wherein the extended section of the elongated housing acts as a handle for the user to hold such that the last sealed compartment may be opened easily.

8. A multiple applicators as in claim 1, wherein said elongated housing further comprises of one end that extends beyond the sealed end of the last sealed compartment wherein the extended section of the elongated housing acts as a handle for the user to hold such that the last sealed compartment may be opened easily.

9. A multiple applicators comprising:
    an elongated housing that is separated into multiple sealed compartments along its length;
    one or more of the sealed compartments encloses an elongated member with a free end and another end affixed to one end of the sealed compartment; and
    an opening means located at one or more of said sealed compartments near said free end of said elongated member and near an end of each sealed compartment away from the end near the opening means in the adjacent sealed compartments wherein said sealed compartment may be opened and removed;
    wherein said elongated housing may be selectively severed into shorter sections at the opening means.

10. A multiple applicators as in claim 9, wherein said elongated housing further comprises of one end that extends beyond the sealed end of the last sealed compartment wherein the extended section of the elongated housing acts as a handle for the user to hold such that the last sealed compartment may be opened easily.

11. A multiple applicators as in claim 9, wherein a holder is provided comprising an elongated hollow tube or an elongated member with one or more holes at its end to hold the severed section of the elongated housing for application.

12. A multiple applicators comprising:
    an elongated housing that is separated into multiple sealed compartments along its length;
    one or more of the sealed compartments encloses an elongated member with a free end and another end affixed to one end of the sealed compartment; and
    an opening means in the form of a score line located at one or more of said sealed compartments near said free end of said elongated member wherein said sealed compartment may be opened and removed;
    wherein said elongated housing may be selectively severed into shorter sections at the opening means.

13. A multiple applicators as in claim 12, wherein one or more of said sealed compartments enclose a liquid or a viscous substance.

14. A multiple applicators as in claim 12, wherein said elongated housing further comprises of one end that extends beyond the sealed end of the last sealed compartment wherein the extended section of the elongated housing acts as a handle for the user to hold such that the last sealed compartment may be opened easily.

15. A multiple applicators as in claim 9, wherein one or more of said sealed compartments enclose a liquid or a viscous substance.

16. A multiple applicators as in claim 15, wherein said elongated housing further comprises of one end that extends beyond the sealed end of the last sealed compartment wherein the extended section of the elongated housing acts as a handle for the user to hold such that the last sealed compartment may be opened easily.

17. A multiple applicators comprising:
- an elongated housing that is separated into multiple sealed compartments along its length;
- one or more of the sealed compartments encloses an elongated member with a free end and another end affixed to one end of the sealed compartment;
- an applicator tip affixed to said free end of said elongated member; and
- an opening means located at one or more of said sealed compartments near said applicator tip and near an end of said sealed compartment away from the end near the opening means in the adjacent sealed compartments wherein said sealed compartment may be opened and removed;
- wherein said elongated housing may be selectively severed into shorter sections at the opening means.

18. A multiple applicators as in claim 17, wherein a holder is provided comprising an elongated hollow tube or an elongated member with one or more holes at its end to hold the severed section of the elongated housing for application.

19. A multiple applicators comprising:
- an elongated housing that is separated into multiple sealed compartments along its length;
- one or more of the sealed compartments encloses an elongated member with a free end and another end affixed to one end of the sealed compartment;
- an applicator tip affixed to said free end of said elongated member; and
- an openings means in the form of a score line located at one or more of said sealed compartments near said applicator tip wherein said sealed compartment may be opened and removed;
- wherein said elongated housing may be selectively severed into shorter sections at the opening means.

20. A multiple applicators as in claim 19, wherein one or more of said sealed compartments enclose a liquid or a viscous substance.

21. A multiple applicators as in claim 19, wherein said elongated housing further comprises of one end that extends beyond the sealed end of the last sealed compartment wherein the extended section of the elongated housing acts as a handle for the user to hold such that the last sealed compartment may be opened easily.

22. A multiple applicators as in claim 17, wherein one or more of said sealed compartments enclose a liquid or a viscous substance.

23. A multiple applicators as in claim 22, wherein said elongated housing further comprises of one end that extends beyond the sealed end of the last sealed compartment wherein the extended section of the elongated housing acts as a handle for the user to hold such that the last sealed compartment may be opened easily.

24. A multiple applicators as in claim 17, wherein said elongated housing further comprises of one end that extends beyond the sealed end of the last sealed compartment wherein the extended section of the elongated housing acts as a handle for the user to hold such that the last sealed compartment may be opened easily.

* * * * *